United States Patent [19]

Scheer et al.

[11] Patent Number: 5,912,174
[45] Date of Patent: Jun. 15, 1999

[54] STEM CELL AND LYMPHOCYTE STORAGE

[76] Inventors: David Scheer, 51 Sage Hollow Rd., Guilford, Conn. 06437; Bernard M. Babior, 4295 Ibis St., San Diego, Calif. 92103

[21] Appl. No.: 08/559,894

[22] Filed: Nov. 20, 1995

Related U.S. Application Data

[63] Continuation of application No. 07/903,858, Jun. 25, 1992, abandoned.

[51] Int. Cl.$^6$ .............................. C12N 5/00; A61K 35/14
[52] U.S. Cl. .............................. 435/374; 435/2; 435/325; 424/93.7; 424/529
[58] Field of Search .............................. 435/240.2, 240.3, 435/2, 182, 948, 325, 374, 93.7, 529; 424/93.7, 529

[56] References Cited

U.S. PATENT DOCUMENTS

| | | | |
|---|---|---|---|
| 4,639,373 | 1/1987 | Babior | 435/2 |
| 4,923,797 | 5/1990 | Babior | 435/2 |

FOREIGN PATENT DOCUMENTS 2 600 671   12/1987   France.

OTHER PUBLICATIONS

Chmiel et al., Biomedizinische Technik 25:52–57, 1980.
Abstract No. 2034029, English translation of Abstract of Chmiel et al., Biomedizinische Technik 25:52–57, 1980.
Kohsaki et al., Stem Cells, 1:111–123, 1981.
Delforge et al., British J. Haematol., 53:49–54, 1983.
Lasky et al. Transfusion, 26:331–334, 1986.
Vellekoop et al., Exp. Hematol., 11(Suppl. 14):71, Abs. #130, 1983.
Smith et al., British Journal of Haematology, 68, pp. 29–34 (1986).

*Primary Examiner*—Michael G. Wityshyn
*Assistant Examiner*—Janet M. Kerr
*Attorney, Agent, or Firm*—Fish & Richardson, P.C.

[57] ABSTRACT

Methods of stabilizing lymphocytes and/or stem cells obtained from a mammal by suspending them in an aqueous medium comprising gelatin.

16 Claims, 1 Drawing Sheet

STEM CELL AND LYMPHOCYTE STORAGE

This is a continuation of application Ser. No. 07/903,858, filed Jun. 25, 1992, now abandoned.

BACKGROUND OF THE INVENTION

This invention relates to storing stem cells and phocytes without unacceptable loss of cell function.

Stem cells are undifferentiated cells which are pluripotent—i.e., they can differentiate into cells which have diverse functional characteristics. They are not fully differentiated, and they retain the ability to duplicate. Of particular interest are lymphohematopoietic stem cells which differentiate into lymphoid and myeloid cells. Lymphohematopoietic stem cells include the following cells, as well as many others: a) cells that are colony-forming cells for granulocytes/monocytes (CFU-GM); b) cells that are colony-forming for erythrocytes (BFU-E); c) colony-forming cells for eosinophiles (CFU-Eo); d) multipotent colony forming cells (CFU-GEMM); e) immature lymphoid precursor cells, including precursors of B-cells and T-cells; and f) pluripotent stem cells. FIG. 1 is a commercially distributed chart depicting the various cells including stem cells involved in hematopoiesis.

Stem cells are essential for transplantation, for example, bone marrow transplantation. Typically bone marrow transplants involve harvesting marrow cells, washing them with a buffer to remove undesired cells and material (e.g., T-cells and/or malignant cells), and suspending then in a suitable medium (e.g. RPMI, autologous serum, and DMSO). The resulting material is either immediately infused into the recipient or it is cryopreserved (frozen well below 0° C.) for later use. Peripheral blood stem cells are also used for bone marrow transplantation. Stem cells are obtained from peripheral blood by leukapheresis, with similar subsequent processing.

Civin (U.S. Pat. Nos. 4,714,680; 4,965,204; and 5,035,994) describes a monoclonal antibody specific for an antigen on human pluripotent lymphohematopoietic stem cells, and not for antigens on normal mature human lymphoid and myeloid cells. Tsukamoto et al. (U.S. Pat. No. 5,061,620) describe human hematopoietic stem cells, their separation, characterization, and use. Each of those patents is hereby incorporated by reference. These and other rapidly advancing technologies may make bone marrow transplants and other medical procedures available to a far larger patient population than can currently receive this treatment.

The lymphocyte family includes lymphoid stem cells as well as the differentiated cells resulting from them (T-cells, B-cells, and plasma cells). See FIG. 1. In various situations, it is desirable to obtain cell populations enriched in certain lymphocytes and/or depleted in others. For example, it may be desirable to destroy a certain population of malignant or infected lymphocytes. Alternatively, it may be desirable to activate a patient's lymphocytes outside the body (e.g., with IL-2) and then to reinfuse them. In short, various technologies are known for treating and/or engineering stem cells or lymphocytes outside the body, and returning the treated cells to the body. Finally, for patients in remote locations, it may be necessary to ship lymphocytes to remote locations for histocompatibility testing in preparation for a transplant, requiring storage during shipment.

Various technologies are known for segregating or selectively enriching or destroying populations of lymphocytes or stem cells, in addition to the technologies mentioned above. For example, other techniques include the CEPRATE™ stem cell concentrator sold by CellPro, Inc. of Seattle, Wash., panning techniques, cell sorting (e.g. fluorescent antibody cell sorting (FACS)), and the use of magnetic beads.

There is a particular need for a convenient and effective way to store stem cells and/or lymphocytes after they are obtained (e.g., in the manner described by Tsukamoto et al.) and before they are used.

SUMMARY OF THE INVENTION

The invention features methods of stabilizing stem cells or lymphocytes obtained from a mammal (particularly human) by suspending them in an aqueous mixture (or storage composition) comprising gelatin.

In preferred embodiments, the cells are suspended in such a mixture for a period in excess of 24 (most preferably in excess of 36, 48, 60 or even 72) hours, preferably at a temperature between freezing and 25° C. Modified fluid gelatin is preferred, but unmodified gelatin may also be used. Any stem cells or lymphocytes may be stored by this method, but the above-mentioned lymphohematopoietic cells (particularly pluripotent stem cells) are particularly suited for the storage technique. The preferred medium comprises gelatin at a concentration such that the storage composition (including the cells) does not gel below 40° C. (e.g. 6–25 percent by weight modified fluid gelatin), and the stem cells are present during storage. Preferably, the mixture comprises a standard cell tissue growth medium. As described below, in preferred applications, the mixture is pharmaceutically acceptable for administration to a human patient. Plasma is optional and the invention may be used with a mixture that has substantially no plasma and may even consist essentially of cell growth medium or buffer, gelatin, and the cells being stored. However, plasma may be advantageous, and it is possible to practice the invention using a medium that comprises 10–75 percent by weight plasma. The cells being suspended may be enriched for a desired cell subpopulation, in comparison to the original sample, e.g., of bone marrow or from leukapheresis.

Other features and advantages of the invention will be apparent from the following description of preferred embodiments and from the claims.

DESCRIPTION OF THE PREFERRED EMBODIMENT(s)

Figure 1:
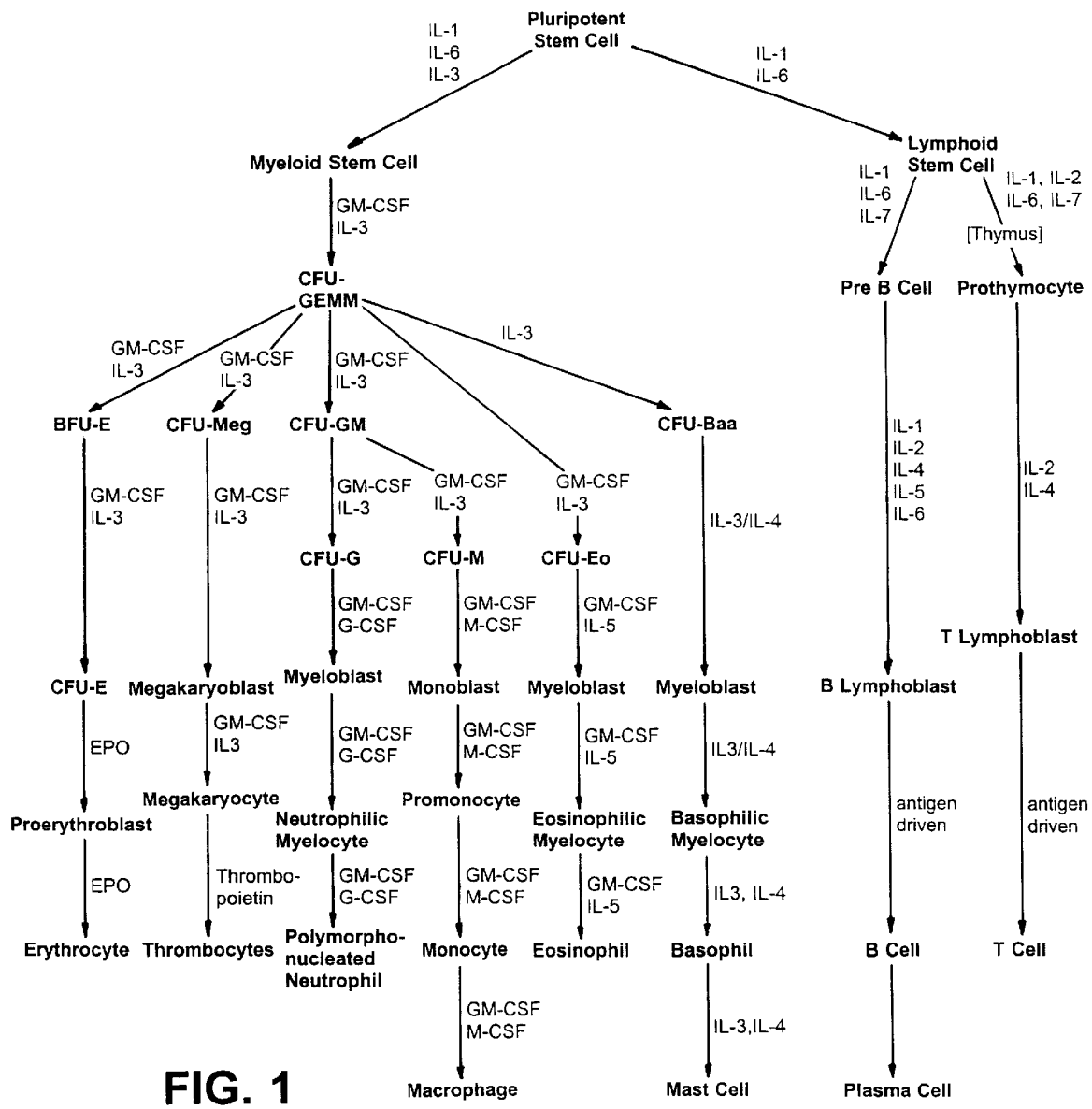
FIG. 1 is a commercially distributed chart depicting the various cells including stem cells involved in hematopoiesis.

The following description of preferred embodiments of the invention is intended to illustrate, not to limit, the invention.

I. Stem Cells

Those skilled in the field will understand that there are known methods of obtaining stem cells that can be suitably stored for later use. The stem cells can be obtained either from bone marrow or from peripheral blood. The stem cells can be purified by known techniques, using for example the technique disclosed in the Tsukamoto et al. patent or the Civin patent, each of which is cited above and hereby incorporated by reference. Other such techniques are also cited above. The invention can be used to store mixed stem cell preparations such as unmodified bone marrow or leukapheresis-derived preparations. It may also be used to store preparations derived from unmodified bone marrow or leukapheresis-derived preparations by selective stem cell or other cell enrichment, e.g., using methodology described above, such as the CEPRATE™ system by CellPro, Inc., Seattle Washington, which is an immunoaffinity separation system.

While the above discussion is generally directed to lymphohematopoietic stem cells and particularly to pluripotent stem cells, other types of stem cells can be stored by the method of the invention, including neurostem cells, epithelial stem cells and others. Those skilled in the art will be able to obtain such cells by known techniques.

II. Lymphocytes

Those skilled in the art are aware of numerous monoclonal antibodies which discriminate between various lymphocytes based on cell surface markers. These antibodies can be used in the various immunologically based cell separation techniques described above to selectively enrich or deplete populations obtained from bone marrow or leukapheresis for specific lymphocytes. Peripheral blood treated in standard ways can be used to recover the mixtures (e.g. buffy coats) from which the lymphocyte subpopulations are purified.

III. Storage Mixtures or Compositions

The preferred storage mixtures use modified fluid gelatin generally as described by Babior (U.S. Pat. No. 4,923,797, which is hereby incorporated by reference. Modified fluid gelatin has been used clinically as a plasma substitute or expander and is widely available under a variety of tradenames, such as PlasmaGel, Haemaccel, Leukogel, Gelofusine, etc. In general, these materials are partly hydrolyzed gelatins which have an average molecular weight from 15,000–40,000 daltons and which form aqueous solutions having a viscosity less than that of a gelatin solution of the same concentration. In some cases they are succinylated, or they are reacted to form urea linkages (for instance), or cross-linked. The commercially available materials usually are in the form of a solution of the modified gelatin in a buffer together with various salts and other ingredients. The term "modified fluid gelatin" as used herein refers to the partly hydrolyzed gelatin component itself whether or not further reacted. In some cases the commercially available solutions can be used, but preferably the partly hydrolyzed gelatin component is purified by separation from the remaining ingredients of the commercial product.

Preferred mixtures include standard tissue cell culture growth media such as RMPI or Eagle's media. It may also be possible to use conventional buffer solutions that provide isotonicity in the compositions of the present invention; for example, common buffers, e.g., Hank's balanced salt solution. Optionally, it may be possible to add a heterocyclic base to the storage mixture as described by Babior (U.S. Pat. No. 4,923,797).

Optionally, plasma can be added to the mixture (or it can be retained from the original patient sample). The plasma may be normal human plasma, either autologous or heterologous with the cells being stored, preferably autologous. If plasma is used, the amount of plasma present in the composition can be 10–75 percent by weight based on the total composition exclusive of the cells.

The amount of modified fluid gelatin in the composition may vary considerably, from 4% by weight based on the total compositions, exclusive of the cells being stored, up to the amount which causes the composition to set to a gel at 40° C. The amounts required for optimum results vary depending upon the source of the modified fluid gelatin but can readily be determined in any given case by a simple test.

Optionally, cell-specific growth factors may be added as needed to preserve cell viability, depending on the desired cell type.

The stem cells or lymphocytes can be dispersed in the composition in suitable amounts. During storage of the stem cell or lymphocyte-containing composition, it is preferably maintained at a temperature below 8° C. although higher temperatures up to 25° C. can be tolerated for relatively short times. For optimum storage life, storage temperature should be maintained at 4° C. or lower, but not below freezing temperature.

After storage the composition containing the stem cells or lymphocytes can be administered after warming without further processing; or if desired the stem cells can be separated from the compositions by washing or centrifuging in order to permit dispersion of the cells in any other desired medium.

It is contemplated that the present invention may be practiced by supplying to blood banks, laboratories or other entities a stock solution suitable for mixing with a suspension of cells to be stored, with directions for mixing the stock solution with the suspension in suitable proportions. Such a stock solution comprises a tissue culture medium or other buffer solution as described above, containing an amount of modified fluid gelatin from about 4–8% by weight up to the amount causing the solution to gel at room temperature, preferably 20 to 40% by weight. Other optional ingredients described above may be included.

An alternate storage medium uses gelatin as generally described by Babior (U.S. Pat. No. 4,639,373) which is hereby incorporated by reference. In this embodiment, the buffer employed can be any conventional tissue culture medium or non-toxic buffer as described above. For best results, the cells in the gelatin-containing buffer should be stored at low temperature, e.g., below 8° C., although they may be stored at higher temperatures up to about 25° C. for at least 12 hours with satisfactory results.

Gelatin from any of the usual commercial sources can be used in the practice of the present invention. The amount of gelatin may vary over a wide range, depending in part on the length of storage desired. There is no critical upper limit on the amount used, except that it must be low enough so that the composition is a liquid, rather than a gel, at a temperature no higher than 40° C. in order to facilitate removal of the gelatin after storage.

If plasma is employed, it can be normal human plasma or autologous plasma. The amount of plasma may vary from 10% by weight of the total composition to as much as 75% by weight.

III. Use of Stored Cells.

After storage, the stem cells can be transfused without further processing except for warming to a temperature no higher than 40° C. to liquefy any gel which is present; or the cells can be reconstituted for use simply by washing out the gelatin and plasma (if any) with buffer which can be the same as or different from the buffer used for storage, or by removal of the gelatin-containing buffer by centrifugation followed by resuspending the stem cells in a desired buffer or medium.

What is claimed is:

1. A method of storing a population of mammalian cells wherein said population of mammalian cells comprises cells which are capable of duplication and differentiation into terminally differentiated lymphoid or myeloid cells, said method comprising providing said population of mammalian cells; and maintaining said population of mammalian cells in suspension in an unfrozen gel for a period in excess of 24 hours, at a temperature below 25° C., said gel being formed from an aqueous mixture comprising gelatin in an amount less than that which causes said aqueous mixture to gel at 40° C., wherein the maintained population of mammalian cells comprises cells which retain the ability to divide and differentiate after maintenance for said period; and said method further comprising prior to removal of the population of cells from suspension the step of enriching said population of mammalian cells for said cells which are capable of duplication and differentiation into terminally differentiated lymphoid or myeloid cells.

2. The method of claim 1 in which said gelatin is modified fluid gelatin.

3. The method of claim 1 in which said aqueous mixture further comprises tissue growth medium.

4. The method of claim 1 in which said cells which are capable of duplication and differentiation into terminally differentiated lymphoid or myeloid cells are pluripotent stem cells.

5. The method of claim 1 wherein said gelatin is present in said aqueous mixture in an amount between four percent and forty percent by weight.

6. The method of claim 1 in which said gelatin is between 1 percent and 25 percent by weight of said aqueous mixture.

7. The method of claim 1 in which said aqueous mixture is pharmaceutically acceptable for administration to a human patient.

8. The method of claim 1 wherein said cells which are capable of duplication and differentiation into terminally differentiated lymphoid or myeloid cells are lymphohematopoietic stem cells.

9. The method of claim 1 wherein said cells which are capable of duplication and differentiation into terminally differentiated lymphoid or myeloid cells are lymphoid stem cells.

10. The method of claim 1 wherein said cells which are capable of duplication and differentiation into terminally differentiated lymphoid or myeloid cells are CFU-GM cells.

11. The method of claim 1 further comprising the step of warming said mixture comprising said population of mammalian cells after storage to liquify gelatin therein, and recovering said population of mammalian cells from the mixture.

12. The method of claim 11 wherein said population of mammalian cells is administered to a human patient after being recovered from said unfrozen gel.

13. The method of claim 1 wherein said cells which are capable of duplication and differentiation into terminally differentiated lymphoid or myeloid cells are BFU-E cells.

14. The method of claim 1 wherein said mammalian cells which are capable of duplication and differentiation into terminally differentiated lymphoid or myeloid cells are CFU-Eo cells.

15. The method of claim 1 wherein said mammalian cells which are capable of duplication and differentiation into terminally differentiated lymphoid or myeloid cells are CFU-GEMM cells.

16. A method of enriching and storing a population of mammalian cells wherein said population of mammalian cells comprises cells which are capable of duplication and differentiation into terminally differentiated lymphoid or myeloid cells, said method comprising providing said population of mammalian cells; enriching said population of mammalian cells for said cells which are capable of duplication and differentiation into terminally differentiated lymphoid or myeloid cells; and maintaining the enriched population of mammalian cells in an unfrozen gel for a period in excess of 24 hours, at a temperature below 25° C., said gel being formed from an aqueous mixture comprising gelatin in an amount less than that which causes said aqueous mixture to gel at 40° C., wherein the maintained enriched population of mammalian cells comprises cells which retain the ability to divide and differentiate after maintenance for said period.

* * * * *